United States Patent [19]

Allman

[11] 4,068,021

[45] Jan. 10, 1978

[54] METHOD OF MAKING GAS ANALYZING ELEMENT

[75] Inventor: Charles E. Allman, San Jose, Calif.

[73] Assignee: Dictaphone Corporation, Rye, N.Y.

[21] Appl. No.: 664,955

[22] Filed: Mar. 8, 1976

Related U.S. Application Data

[62] Division of Ser. No. 513,418, Oct. 9, 1974, Pat. No. 3,959,764.

[51] Int. Cl.$^2$ .......................................... H01C 13/00
[52] U.S. Cl. .................................. 427/116; 23/254 E; 23/255 E; 23/288 F; 23/288 FC; 252/520; 338/34; 427/77; 427/78; 427/101; 427/105; 427/376 A; 427/178
[58] Field of Search ................ 338/34, 296; 23/254 E, 23/255 E, 288 F, 288 FC; 427/77, 78, 125, 126, 116, 101, 376, 105, 178; 106/55; 252/520, 518

[56] References Cited

U.S. PATENT DOCUMENTS

| 2,416,864 | 3/1947 | Bricker | 427/103 |
| 3,029,360 | 4/1962 | Etter | 427/77 |
| 3,092,799 | 6/1963 | Baker | 338/34 |
| 3,138,948 | 6/1964 | Pfefferle | 23/254 E |
| 3,450,565 | 7/1969 | Theodosopoulos | 427/116 |
| 3,564,474 | 2/1971 | Firth et al. | 338/25 |

OTHER PUBLICATIONS

Gingrande A., "Self-Insulating Heating Coil", Western Electric Tech. DIG. No. 23, (7-1971), p. 23.

Primary Examiner—Ralph S. Kendall
Assistant Examiner—John D. Smith
Attorney, Agent, or Firm—Limbach, Limbach & Sutton

[57] ABSTRACT

A catalytic combustion-type, gas sensing, resistive element and the method of making it by forming an electrical conductor, whose electrical resistance varies with temperature, into a helical coil, coating the coil with a refractory material whose coating matures at a temperature in the range of 1200° C to 1400° C, and heating the coated coil at that temperature range until the coating matures and shrinks into a dense, gas-tight sheath about the helical coil. The coating on the helical coil is integral between adjacent loops and there is a hollow space along the longitudinal axis of the coil. The exterior of the sheath coating may then be further coated with a catalyst, catalytic wash coating, or in some embodiments the hollow space is filled with a porous catalytic material such as platinum and the ends of the hollow space are capped with a porous refractory ceramic material. In these and other embodiments a porous refractory ceramic material may also be applied over the catalytic surface to allow combustible gases and oxygen to diffuse into the catalytic surface while protecting the catalytic surface from airborne materials which would otherwise render it inactive. A compensating element is made by the same method but is coated with a non-reactive, non-catalytic material. In the preferred embodiments the refractory coating material contains primarily alumina with small and equal amounts of manganese dioxide and titanium dioxide.

11 Claims, 8 Drawing Figures

METHOD OF MAKING GAS ANALYZING ELEMENT

This is a division of application Ser. No. 513,418, filed October 9, 1974, now U.S. Pat. No. 3,959,764, issued May 25, 1976.

BACKGROUND OF THE INVENTION

The present invention relates to a sensing element in a catalytic combustion-type gas analyzer and more particularly to the resistive sensing element of a gas analyzer of the Wheatstone bridge type. In one species of gas analyzers a resistive heating element, which is one arm of a Wheatstone bridge, is coated with a catalytic material. In the presence of a combustible gas, an exothermic catalytic reaction occurs which heats the element and thus changes its resistive characteristics and unbalances the bridge. A compensating element is utilized as another arm of the Wheatstone bridge in order to balance the effects of the ambient conditions upon the active sensing element. Such a system is described in detail in U.S. Pat. No. 3,586,486 (Kim) and typical prior art gas sensing elements are further depicted in U.S. Pat. Nos. 3,200,011, 3,117,843 and 3,092,799 (Baker). In some prior art sensing elements, such as those described in the above-referenced Baker Patents, a resistive filament is coated with a refractory material to form a bead around the entire coiled filament, with no hollow space in the center of the coil. One of these filament beads is then coated with a catalyst material on the outside of the refractory coating to form the sensing element and another filament bead is coated with an inert material to act as the compensating element.

There are many problems with such prior art sensing elements. They are sensitive to shock and vibration. In some cases the refractory ceramic bead coating is too thick and therefore gives a slow time response. Furthermore, since the filament bead must be heated electrically in order to operate, the thick refractory ceramic coating poses a thermal barrier which requires extra power to operate the instrument.

Still another problem with such prior art bead-type sensing elements is that the refractory coating is inherently porous, allowing poisoning chemicals to enter the bead and chemically attack the filament and also allowing the filament to evaporate or diffuse through the porous coating. One reason for this porosity defect is that typically the refractory coatings do not fully mature or cure at a temperature which is below the melting point of the filament material, which in the case of platinum is approximately 1750° C. This structure is weak for the same reason.

At the maturing temperature ranges to which some prior art coatings must be heated excessive grain growth in the conductive wire (filament) takes place which results in a severe weakening of the filament as well as a change in its electrical resistance characteristics. Both of these results are highly undesirable since they lead to a short performance life and inaccuracies.

One prior art device attempted to overcome this problem by first coating the filament with a ceramic material and then bending the ceramically coated material into a helical coil. The coil is then coated with glass. The purpose of the glass is to seal the cracks which are inherent in the ceramic coating on the filament. These cracks developed first of all, due to incomplete maturing and secondly, due to the fact that the bending of the wire into the helix forms further minute cracks. It is difficult to produce an effective sealing even with the glass because after the coil is dipped into the molten glass a ceramic coating is next applied over the glass and the element is heated. The voids or cracks in the original ceramic coating cause further voids or cracks in the glass coating which blow out under the heat of the maturing process for the outer ceramic coating and form still further cracks. Still another problem in using glass as a sealing agent is that the silica of the glass will leak through the cracks in the filament ceramic coating to react with the platinum filament in a reducing atmosphere to form platinum silicide. This reaction changes the resistive characteristic of the wire filament, thereby causing inaccuracy in the measuring instrument. Furthermore, the silica from the glass will migrate outwardly to seal off the outer catalyst coating, causing long-term deterioration.

Still another problem of many prior art sensing elements is that the porosity of the ceramic coating allows growth of a conductive crystal between the helical coils of the filament, which tends to short out adjacent loops of the filament and thereby causes inaccuracy in the sensor readings.

SUMMARY OF THE INVENTION

The above and other disadvantages of the prior art are overcome by the present invention of a catalytic combusion-type gas analyzer sensor and a method of making it, which comprise forming a length of electrically conductive material, whose resistance varies with temperature, into a helical coil, coating the coil with a refractory material, and heating the coated coil at a predetermined temperature, in the range of 1200° C to 1400° C in one embodiment, until the coating material matures into a thin walled, gas-tight, dense sheath which is in snug engagement with the filament to form a hollow cylinder. The coating is integral between adjacent loops of the coiled filament. The coated sensing element is thereafter either coated with a catalyst on its exterior surface or, in some embodiments, a core of catalytic material is packed into the hollow space formed by the coated, coiled filament. In still other embodiments both forms of supporting the catalyst are utilized. The core of catalytic material which is packed into the hollow space of the coated filament is preferably porous, such as platinum wool or wire and in some embodiments porous end caps are formed over the hollow space to prevent certain airborne materials from poisoning the catalyst material.

In these and other embodiments a porous refractory ceramic material is preferably applied over the catalytic surface. The porosity of this material allows combustible gases and oxygen to diffuse into the catalytic surface, yet it will provide protection to the catalytic surface from airborne materials which render the catalytic surface inactive.

The particular airborne materials contain elements such as silicon, lead, and phosphorus. These materials react on hot surfaces and would be deposited on the porous protective coating rather than the catalytic surface beneath, thereby extending the useful life of the catalytic element. The term poisonous as used herein is to be understood as meaning a material which reacts chemically with the catalyst, or which coats it, to render it ineffective.

In the preferred embodiment, the refractory coating includes an oxide of aluminum, such as $Al_2O_3$ (alumina). In one preferred embodiment the coating further includes manganese dioxide (MnO$_2$) and titanium dioxide (TiO$_2$) in equal proportions to each other and which together make up about 1.0% to 6.0% by weight of the total composition of the coating material. In other preferred embodiments, magnesium oxide (MgO) is also added to control grain growth.

The specific steps of the method of making the refractory coating according to one embodiment of the invention comprise combining predetermined amounts of alumina, manganese dioxide and titanium dioxide with water and hydrochloric acid, milling this basic combination for a predetermined period of time until the mixture is deflocculated, and then removing a portion of the water, as for example 75% of the water, by heating the mixture to a creamy consistency. In still other embodiments a small amount of manganese oxide, a deflocculating agent, such as a particular type of fish oil, and organic solvents, to aid in the application of the coating to the coiled filament, are added to the basic mixture.

It is therefore an object of the present invention to provide a gas analyzer sensing and/or compensating element which has a resistive filament coated with a refractory material which fully matures at a relatively low temperature to form a gas-tight seal;

It is another object of the invention to provide a gas analyzer sensing and/or compensating element which has a resistive filament coated with a refractory material which fully matures at a temperature low enough and at a fast enough rate to prevent excessive grain growth in the resistive filament;

It is another object of the invention to form a resistive element, combustible gas sensor which does not utilize any compounds containing or having the ability to form silica;

It is still another object of the invention to form a combustible gas sensor which is both resistant to physical shock and which is light in weight;

It is a further object of the invention to form a catalytically coated, resistive element, combustible gas sensing device which is resistant to poisoning of the catalyst by certain materials;

It is a still further object of the invention to provide a resistive element gas sensing device which is not subject to either evaporation or diffusion of the resistive element within the device.

The foregoing and other objectives, features and advantages of the invention will be more readily understood upon consideration of the following detailed description of certain preferred embodiments of the invention, taken in conjunction with the accompanying drawings.

DETAILED DESCRIPTION OF CERTAIN PREFERRED EMBODIMENTS

Figure 1:
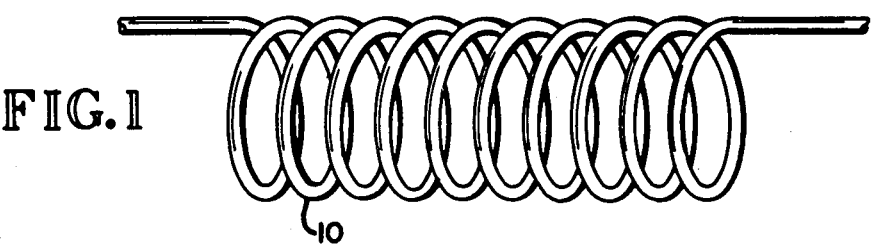
FIG. 1 is an enlarged side view, in elevation, of a coiled resistive element for the sensor according to one embodiment of the invention.
Figure 2:
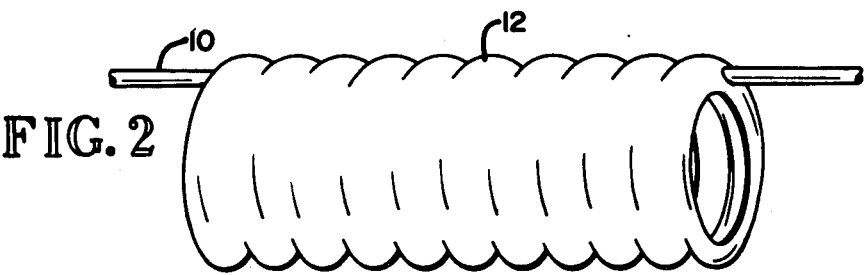
FIG. 2 is an enlarged side view, in elevation, of the coil of FIG. 1 after having been coated with unmatured refractory material according to the invention.
Figure 3:
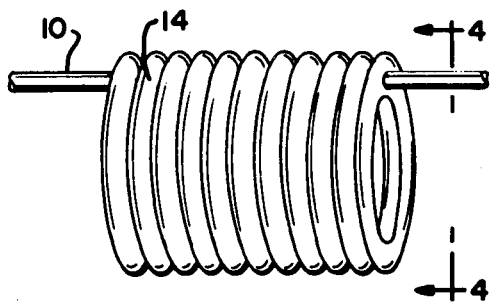
FIG. 3 is an enlarged side view, in elevation, of the coated coil of FIG. 2 after maturation of the refractory coating by heating.
Figure 4:
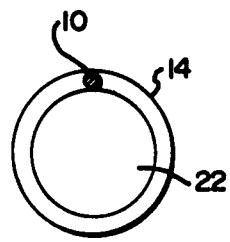
FIG. 4 is an enlarged end view, in elevation, taken generally along the lines 4—4 in FIG. 3.

Referring now more particularly to FIG. 1 of the drawings, there is depicted a helical coil 10 made of a conductive material, such as platinum, whose electrical resistance varies with temperature. Other suitable coil filaments, by way of example only, are a platinum/iridium alloy or also a platinum/rhodium alloy.

The helically coiled filament is then coated with a refractory material 12 which is in a liquid form. The coated element is placed inside an insulated environment, such as a furnace, and heated to a predetermined high temperature in the range of from 1200° C to 1400° C. The coated coil may also be heated, for example, by passing an electric current through the helical filament 10 to raise its temperature by resistive heating to the required value.

As the refractory coating matures during the heating, sintering takes place to produce a dense refractory sheath. The sintering process amounts to a shrinking of the coating by 25% to 50%. This shrinkage seals the filament 10 in the dense refractory sheath 14. The sheath 14 prevents or greatly attenuates the rate at which the filament 10 is lost by diffusion or by oxidation. The sheath 14 also has greater strength because of its higher density than prior art refractory ceramic coatings of this type which do not fully mature at a temperature range below the melting point of the filament.

Besides the refractory ceramic sheath 14 maturing below the melting temperature of the filament 10, the refractory ceramic sheath also matures at temperatures low enough and also at a fast enough rate to prevent excessive grain growth in the filament 10. Such grain growth (recrystallization) would otherwise result in severe weakening of the wire as well as a change of its electrical resistance.

Figure 5:
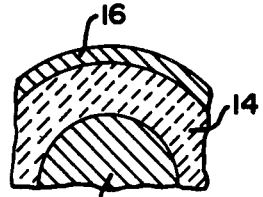
FIG. 5 is a further enlarged view, in cross-section, of a portion of the coated sensing filament depicted in FIG. 3.

Referring now to FIG. 5, the outer surface of the sheath 14 may be further coated with a catalytic layer 16 to form a sensing element which is active, that is, catalytic, in the presence of air and a combustible gas such as H$_2$, CH$_4$, C$_3$H$_8$, CO, and other combustible hydrocarbons, alcohols, ketones, etc., when the catalytic coating 16 is heated to the proper temperature. Such a catalytic caoting may be, for example, a platinum film or any of various types of catalytic wash coatings which are well known in the art.

Figure 6:
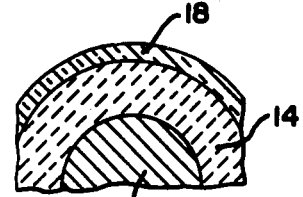
FIG. 6 is an enlarged view, in cross-section, of a portion of a compensating element constructed according to the invention.

For a bridge or Wheatstone-type circuit, a reference element is also needed which has the same electrical and thermal characteristics as the catalytically coated element but which is non-reactive with the combustible gas. For this element a glass coating 18 is applied to the outside of the refractory ceramic coating 14 in place of the catalytic coating 16, as is illustrated in FIG. 6. A suitable bridge circuit for such a sensing and compensating element is described in U.S. Pat. No. 3,586,486 and in numerous other references known to the art.

Because the sheath 14 is relatively thin-walled and dense, the sensing and compensating elements of the present invention are much smaller and lighter than prior art structures. They are also more resistant to damage by shock and vibration. The thin-walled sheath 14 has greater heat conductivity than prior art devices and thereby reduces the power required to maintain a given surface temperature for the element to perform its function. This reduction in power will result in a longer battery life, when batteries are used to power the source. Furthermore, the lower thermal mass of the element means that it will have a faster response time to combustible gases and also a faster recovery time. This characteristic is also related to the shorter diffusion path for gases to the active catalytic sites as compared to the more bulky and porous bead-type elements.

Figure 7:
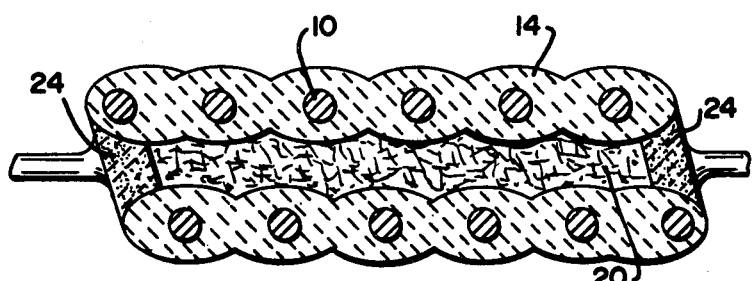
FIG. 7 is an enlarged vertical view, in section, of a second embodiment according to the invention.

Referring now more particularly to FIG. 7, an alternative embodiment to that depicted in FIG. 5 is illustrated in which porous, catalytic material 20 is fitted within the hollow space 22 created by the loops of the coated, coiled filament 10. The porous catalytic material 20 may be platinum wool, platinum sponge, coils of platinum wire, or other type of porous platinum catalyst which is snug fitted against the interior surface of the ceramic coating 14. After the hollow space 22 is packed with a catalyst, the ends of the hollow space are covered with a porous refractory ceramic material 24 to protect the catalytic material 20 from materials that may "poison" it, such as silicon dioxide which will coat the catalytic material to make it non-reactive. Although the embodiment depicted in FIG. 7 does not have an exterior catalytic coating such as the coating 16 depicted in FIG. 5, in other embodiments, a sensing element of the type depicted in FIG. 7 may also have an exterior catalytic coating.

Figure 8:
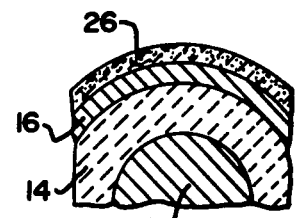
FIG. 8 is an enlarged view, in section, of a portion of a coated sensing filament of a third embodiment of the invention.

The exterior catalytic coating 16 in either the embodiment of FIG. 5 or FIG. 7 may further have an outer porous refractory ceramic coating 26, as depicted in FIG. 8, which allows the combustible gas to diffuse through and react in the presence of the catalytic coating 16 but which prevents poisoning materials, such as silicon, from reaching it as easily by reacting with them at the outer surface of the coating 26. This prolongs the life of the element.

One example of a suitable refractory coating is made by mixing: 24.1 grams of $Al_2O_3$, 0.44 grams of $MnO_2$, 0.44 grams of $TiO_2$ together with 60 ml. of $H_2O$ plus 1 ml. of concentrated HCl. The water gives a liquid base and the HCl acts as a deflocculating agent. This mixture is milled for approximately five hours to achieve deflocculation and then the bulk of the $H_2O$ is removed by a steam bath until the mixture takes on a creamy consistency. The percentage of the oxide elements by weight in the above mixture is approximately 96.5% $Al_2O_3$ and 1.75% each of $MnO_2$ and $TiO_2$, not counting the liquids which are ultimately evaporated. The coating is then brushed onto the coil and the coil is heated, by resistive heating, to a temperature range of 1300° C to 1325° C for approximately five minutes until the coating matures and shrinks, thereby contracting the filament coil loops along the longitudinal axis of the coil.

In a second example the following materials were combined:

| 98 gm. $Al_2O_3$ | 1 gm. $MnO_2$ |
| 1 gm. $TiO_2$ | 1 gm. $Al(NO_3)_3 \cdot 9H_2O$ |
| 245 ml. $H_2O$ | 5 ml. conc. HCl |

This mixture was milled for 24 hours and thereafter the excess water was removed to give the mixture a creamy consistency. The remaining steps of applying and heating the coating as in the above example were then taken. The composition by weight of the dry materials was 98% $Al_2O_3$ and 1% each of $TiO_2$ and $MnO_2$.

In a third example:

| 96.5 gm. $Al_2O_3$ | 1 gm. $Al(NO_3)_3 \cdot 9H_2O$ |
| 1.75 gm. $MnO_2$ | 245 ml. $H_2O$ |
| 1.75 gm. $TiO_2$ | 5 ml. conc. HCl | were combined together and milled for twenty four hours and the excess $H_2O$ was removed as described above. The remaining steps of applying the coating and heating it were undertaken as described above in the first example.

A fourth mixture was comprised of:

| 94 gm. $Al_2O_3$ (94%)* | 245 ml. $H_2O$ | |
| 3 gm. $TiO_2$ (3%) | 5 ml. HCl | |
| 3 gm. $MnO_2$ (3%) | | (*by weight) |

This mixture was milled, applied and heated as in the above examples.

In still other variations of this basic coating, magnesium oxide (0.25% by weight) is added to the mixture to control grain growth, together with a deflocculating agent such as fish oil (known in the trade as Menhaden fish oil-type Z-3) and an organic solvent to give a liquid base. This mixture is milled for approximately 24 hours and then applied to the coiled filament and cured at a temperature range of 1200° C to 1400° C.

While certain recipes for a refractory ceramic coating are given above, it should be apparent that other subtle variations on this recipe may be employed with the same success. The primary factor is that the refractory coating fully mature at a temperature range below the melting point of the filament material and that the matured coating be gas-tight against the filament material without weakening the filament material or changing its electrical characteristics. Furthermore, the temperatures given in the above examples may be lowered slightly if the heating time is lengthened. The primary factor is that the coating be heated until shrinkage takes place and the coating is fully matured.

While in the above examples the percentage by weight of $Al_2O_3$, $MnO_2$ and $TiO_2$ varies from 98% to 94% and 1% each to 3% each, respectively, these amounts may be varied with equal success so that the percentage by weight of $MnO_2$ and $TiO_2$ is each 1% to 6% of the total composition.

The term refractory as used herein is in its usual sense, i.e., a material which is capable of enduring high temperatures, such as in excess of 1000° C., without fusing or otherwise softening.

The terms and expressions which have been employed here are used as terms of description and not of limitation, and there is no intention, in the use of such terms and expressions, of excluding equivalents of the features shown and described, or portions thereof, it being recognized that various modifications are possible within the scope of the invention claimed.

What is claimed is:

1. A method of making a resistive element for a catalytic combustion type gas analyzer comprising the steps of:
    forming a filament of electrically conductive material, whose resistance varies with temperature, into a helical coil, coating the coiled filament with a refractory material, the coating being at least 94% by weight alumina mixed with other refractory oxides, including substantially equal proportions by weight of manganese dioxide and titanium dioxide which together are within the range of 1% to 6% by weight of the total composition of the coating material after maturation, the coating having a maturation temperature range of 1200° C to 1400° C, and heating the coated filament at a temperature in the range of 1200° C to 1400° C until the coating matures to form a dense, gas-tight sheath, in tight engagement with the filament, which is integral between adjacent loops of the helical coil.

2. A method of making a resistive element for a gas analyzer as recited in claim 1, further comprising the steps of preparing the coating of refractory material by combining the predetermined amounts of $Al_2O_3$, $MnO_2$ and $TiO_2$ with a liquid medium and a deflocculating agent, milling the combination for a predetermined time, and removing a portion of the liquid solvent from the mixture until the mixture has a creamy consistency.

3. A method of making a resistive element for a gas analyzer as recited in claim 2 wherein the predetermined amounts of $Al_2O_3$, $MnO_2$ and $TiO_2$ are by weight (of the solids) 96.5% $Al_2O_3$, 1.75% $MnO_2$ and 1.75% $TiO_2$.

4. A method of making a resistive element for a gas analyzer as recited in claim 2 wherein the steps of preparing the coating include adding water as a liquid medium and HCl as a deflocculating agent and milling the mixture for five hours and wherein the steps of heating the coated filament include the steps of heating it to a temperature of from 1300° C to 1325° C for five minutes.

5. A method of making a resistive element for a gas analyzer as recited in claim 1, further comprising the steps of preparing the coating of refractory material by combining the predetermined amounts of $Al_2O_3$, $MnO_2$ and $TiO_2$, with MgO, a deflocculating agent, and a liquid medium, and milling then the combination for a predetermined period of time until the combination is deflocculated.

6. A method of making a resistive element for a gas analyzer as recited in claim 5, wherein the predetermined amounts are 96.25% $Al_2O_3$, 0.25% MgO, 1.75% $MnO_2$ and 1.75% $TiO_2$.

7. A method of making a resistive element for a gas analyzer as recited in claim 1, further comprising the steps of preparing the coating of refractory material by combining the predetermined amounts of $Al_2O_3$, $MnO_2$, and $TiO_2$, with $Al(NO_3)_3 \cdot 9H_2O$, a deflocculating agent, and a liquid medium, and then milling the combination for a predetermined period of time until the combination is deflocculated.

8. A method of making a resistive element for a catalytic combustion type gas analyzer as recited in claim 1 further comprising the step of placing a catalytic material in contact with the surface of the refractory coating.

9. A method of making a resistive element for a catalytic combustion type gas analyzer as recited in claim 1 further comprising the step of coating a catalytic material on the surface of the coating of refractory material.

10. A method of making a resistive element for a catalytic combustion type gas analyzer as recited in claim 1 further comprising the steps of applying a catalytic coating on the refractory coating and applying an outer, porous refractory coating over the catalytic coating, the porous refractory coating having a porosity and thickness just sufficient to allow combustible gases and oxygen to diffuse through it to reach the catalytic coating but to block diffusion through it of airborne catalyst poisoning materials by reacting with the poisoning materials at the outer surface of the porous refractory coating.

11. A method of making a resistive element for a catalytic combustion type gas analyzer as recited in claim 1 further comprising the steps of forming the filament into a helical coil which defines a hollow space along its longitudinal axis prior to the coating step, and packing a core of catalytic material into the hollow space of the filament helix.

* * * * *